United States Patent [19]

Kyle

[11] 4,297,172

[45] Oct. 27, 1981

[54] LOW ENERGY PROCESS OF PRODUCING GASOLINE-ETHANOL MIXTURES

[75] Inventor: Benjamin G. Kyle, Manhattan, Kans.

[73] Assignee: Kansas State University Research Foundation, Manhattan, Kans.

[21] Appl. No.: 114,699

[22] Filed: Jan. 23, 1980

[51] Int. Cl.³ .................. B01D 3/14; C07C 29/26; C07C 31/08
[52] U.S. Cl. .................................. 203/19; 44/53; 44/56; 203/44
[58] Field of Search .................. 203/19, 44, 45, 46, 203/43; 44/53, 56

[56] References Cited

U.S. PATENT DOCUMENTS 2,402,077 6/1946 Patterson ........................... 203/44
2,591,672 4/1952 Catterall ............................ 44/56

Primary Examiner—Frank Sever

[57] ABSTRACT

Gasoline-ethanol mixtures useable as motor fuel are produced by a relatively low energy process comprising interrelated distillation and extraction steps. In the first step, aqueous ethanol, such as an ethanol fermentation beer, is subjected to fractional distillation to produce a distillate of at least 75 weight percent ethanol, which is then subjected to extraction with gasoline under conditions producing an extract containing the desired amount of ethanol, such as 8 to 14% by weight. The aqueous phase raffinate from the extraction is returned to the fractionation column for redistillation.

9 Claims, 2 Drawing Figures

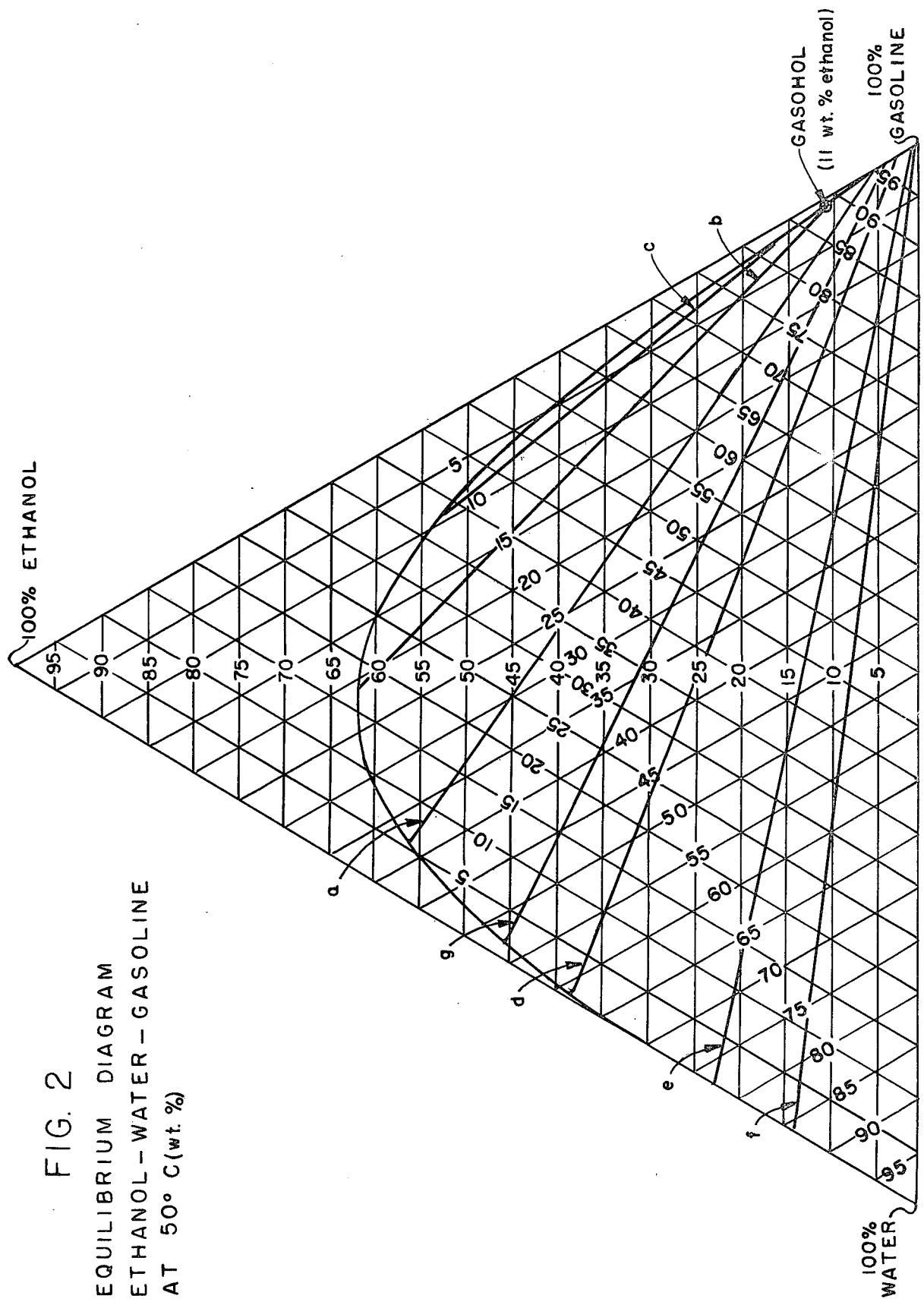

LOW ENERGY PROCESS OF PRODUCING GASOLINE-ETHANOL MIXTURES

BACKGROUND AND PRIOR ART

This invention relates to a process for producing gasohol, which is a blend of gasoline and ethanol containing approximately 10% by volume ethanol. Ethanol can be readily produced by fermentation processes, which yield dilute aqueous solutions of ethanol. The conversion of such ethanol fermentation beer to substantially anhydrous ethanol for blending with gasoline requires large amounts of heat energy for the required distillations. Ordinary fractional distillation can carry the concentration only to the constant boiling mixture, which is approximately 95 weight percent ethanol. For further concentration, azeotropic distillation is required which involves expensive equipment as well as large amounts of heat energy.

The ultimate role of gasohol in the energy future of the United States and other countries depends on whether its production can be made both energetically and economically appealing. However, to date all published energy and economic analyses for the production of gasohol have been predicated on the assumption that anhydrous ethanol would be produced and subsequently blended with gasoline. Because of the difficulty in obtaining anhydrous ethanol, the separational energy requirement plays a major role in determining the total processing energy, and thus the unfavorable economic outlook for gasohol production.

In considering alternative processes for producing gasohol, some consideration has been given to the possibility of extracting dilute aqueous ethanol with gasoline. See The Colorado Gasohol Task Force Report to the United States Department of Agriculture, dated Jan. 31, 1978, entitled "Production and Marketing of Alcohol Motor Fuels from Colorado Agricultural Commodities: A Tentative Description". However, published phase equilibrium data for ethanol-water-hydrocarbon solvent systems show that the transfer of ethanol is unfavorable in such a process. Further, there is no published data on ethanol-water-gasoline extraction systems, the published data relating only to specific hydrocarbons such as specific aliphatic or aromatic hydrocarbons. See, for example, Nowakowska et al, *Ind. Eng. Chem.*, Data Series, 1, 42 (1956); Vold et al, *J. Am. Chem. Soc.*, 54, 4217 (1932); Washburn et al, *J. Am. Chem. Soc.*, 61, 1694 (1939); and Moulton et al, *Ind. Eng. Chem.*, 45, 2350 (1953).

SUMMARY OF INVENTION

The process of the present invention utilizes a combination of distillation and extraction steps to produce gasoline-ethanol mixtures, such as gasohol, with greatly reduced heat energy requirements. In the first step, aqueous ethanol is concentrated by fractional distillation. This concentration does not need to be carried to the constant boiling mixture; for example, distillates of 75 to 90 weight percent ethanol are preferred. Under these conditions, the vapor-liquid equilibrium relationship for the ethanol-water system is quite favorable, and much less heat energy is required for the distillation as compared with carrying the concentration of ethanol by a series of distillations to absolute ethanol. The distillate of the present process of limited ethanol concentration, nevertheless, has a sufficiently high ethanol concentration to adapt it for a favorable extraction with gasoline. By controlling the temperature of the extraction step, a gasoline phase extract product can be obtained with the gasoline-ethanol proportions which make it suitable for motor fuel use. Gasohol containing approximately 10% by volume or 11% by weight ethanol can be produced.

The preferred temperature for the extraction of 40° to 60° C. is readily obtainable without adding heat energy by feeding the condensed distillate directly to the extractor. The aqueous raffinate phase from the extractor is preferably fed to the appropriate section of the distillation column. At 11% ethanol by weight the gasoline phase product from the extractor will contain around 1% by weight water, but this can readily be reduced by known procedures to the level of 0.1% by weight or less, which is acceptable for gasohol. Moreover, the process lends itself to other heat saving and energy efficient relationships. The bottoms from the distillation column can be used to heat the incoming ethanol-water feed stock. If flash distillation is used to reduce the water content of the gasohol product from the extractor, the gasoline-ethanol (e.g. gasohol) condensate product of the flash distillation can be used to heat the gasoline feed to the extractor.

THE DRAWINGS

With reference to the attached drawings, FIG. 1 is a diagrammatic flow sheet illustrating an embodiment of the process of the present invention; and FIG. 2 is an equilibrium diagram comprising a graphic representation of liquid-liquid phase equilibrium data for ethanol-water-gasoline at 50° C.

DETAILED DESCRIPTION

Figure 1:
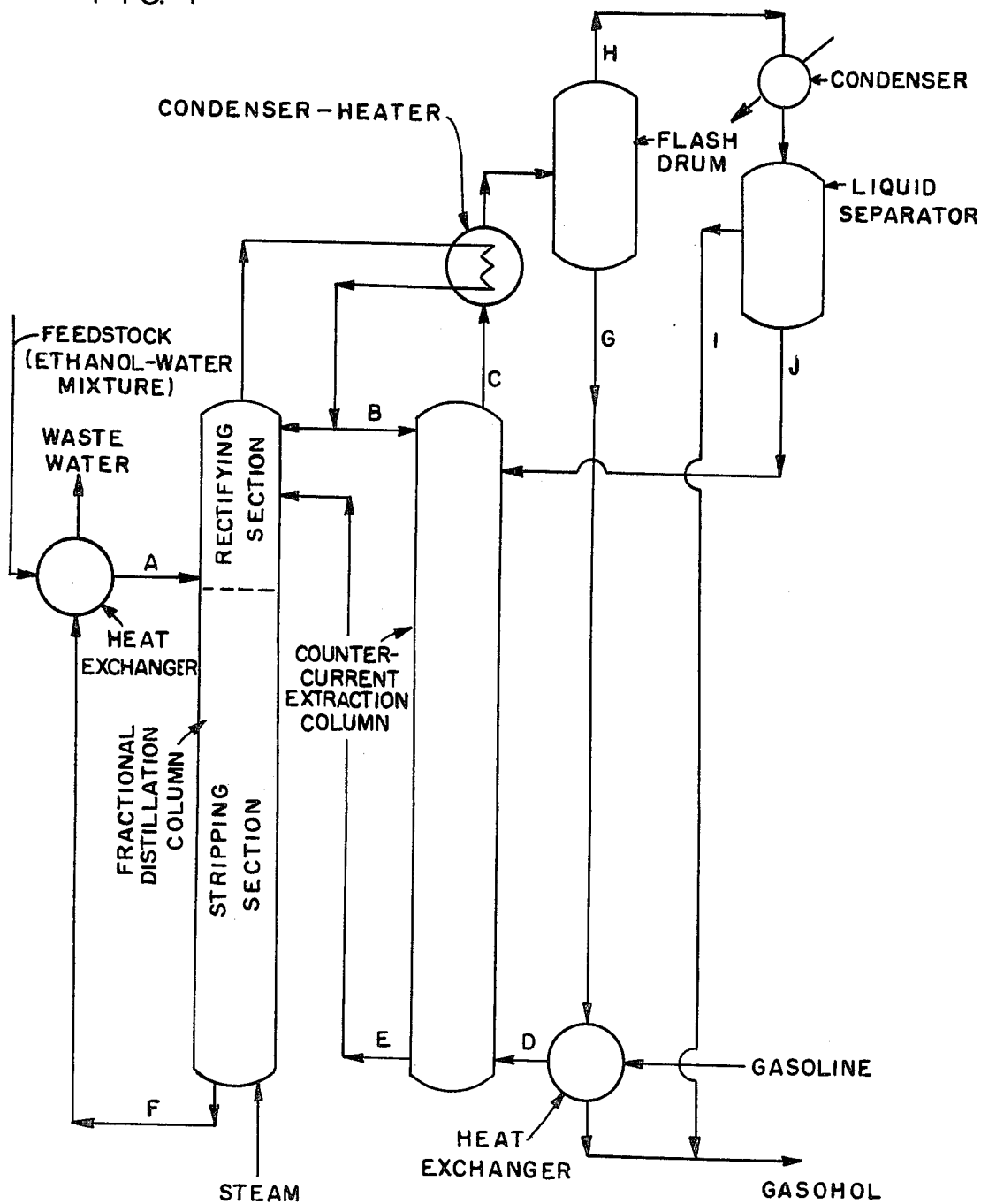

The aqueous ethanol feed stock for practicing the present invention may be obtained from an ethanol fermentation process, such as an aqueous beer having a concentration within the range from 1 to 15 weight percent ethanol. Preferably, however, such a fermentation beer has an ethanol concentration of 6 to 10% by weight. Such fermentation beers comprise an advantageous feed stock for use in practicing the present invention. More generally, the feed stock may comprise any mixture of ethanol and water having an ethanol concentration of from 1 to 70 weight percent. Where the aqueous ethanol is produced in small fermentation plants, and shipped to gasoline manufacturing plants for preparation of the gasohol, the crude fermentation beer may be partially concentrated by distillation at the place of production. For example, the concentration may be increased from the range of 1 to 15% by weight ethanol to a concentration in the range of 50 to 70% ethanol to facilitate shipment.

The first step of the process, comprising the distillation step, is carried out in a conventional fractional distillation column having the usual upper rectification section and lower stripping section. For the purpose of the present invention, the stripping section will be larger and will contain more stages than the rectification section. The number of total stages will depend on the desired concentration of the distillate and the ethanol content of the waste stream from the bottom of the column. For carrying out the distillation step of the present invention, the column should be designed and operated under conditions producing a distillate of from 75 to 95 weight percent ethanol. Preferably, however, the ethanol concentration of the distillate is limited to not over 90%, such as a concentration within the range from 75 to 90% ethanol by weight.

The distillate from the fractionation column is condensed, and the hot liquid condensate is subjected to counter-current multiple stage liquid-liquid extraction with gasoline. This step may be carried out in a counter-current extraction column or in other equivalent equipment, such as a series of mixers and settlers. The number of theoretical extraction stages provided should be sufficient at the selected temperature to produce a product approaching the theoretical equilibrium distribution, and having the approximate desired ratio of ethanol to gasoline, such as 5 to 17 weight percent ethanol, or preferably about 8 to 14% ethanol. Gasohol is a preferred product which is about 10% by volume or 11% by weight ethanol. While the extraction may be carried out at temperatures within the range from 20° to 70° C., or up to 100° C. if pressure is used, temperatures within the range from 30° to 60° C. are preferred. In a desirable embodiment, a temperature of around 50° C. is employed for the extraction, such as a temperature within the range from 45° to 55° C. For example, with a distillate ethanol concentration of 75 to 85% by weight, and using an extraction temperature of about 50° C., a gasoline phase extract can be produced containing around 10% by volume ethanol (about 11% ethanol by weight). From four to six theoretical extraction stages should be sufficient.

The water phase raffinate from the extraction will contain both ethanol and gasoline. It is preferably fed into an appropriate section of the distillation column. Depending on ethanol content, the raffinate may be introduced into either the rectifying or stripping sections, depending on whether the ethanol concentration in the raffinate is more or less than in the feed. The gasoline-ethanol product from the extraction will contain more water than desirable for motor fuel use. For example, the gasoline extract may contain from about 0.8 to 1.2 weight percent water. According to accepted standards, the water content should be reduced to around 0.1% by weight or less. The drying of the extraction product to reduce its water content can be accomplished by various known processes, such as by adsorption, absorption, or distillation. For example, the extractor product may be subjected to simple flash distillation, and, if necessary, to subsequent contact with an adsorbent to reduce the water content to substantially 0.1%.

Illustrative liquid-liquid equilibrium data for an ethanol-water-gasoline system was developed experimentally using temperatures of 25° and 50° C. The gasoline selected for these tests was an unleaded regular gasoline having a motor octane number of 78.8, an API gravity of 63.9, and a boiling range of 92° to 425° F. The gasoline was relatively low in aromatics and is the type of motor fuel normally used in leaded form. Since addition of ethanol increases octane rating, gasohol produced from this type of gasoline could be used as a motor fuel in unleaded form. The resulting equilibrium data are summarized below in Tables A and B. The attached diagram of FIG. 2 comprises a plot of the 50° C. data of Table B.

TABLE A

Liquid-Liquid Equilibrium Data for Ethanol-Water-Gasoline at 25° C.

| Water Phase (weight %) | | | Gasoline Phase (weight %) | | |
| --- | --- | --- | --- | --- | --- |
| Water | Ethanol | Gasoline | Water | Ethanol | Gasoline |
| 22.5 | 66.2 | 11.3 | 0.3 | 5.3 | 94.4 |
| 32.9 | 60.7 | 6.4 | 0.3 | 3.7 | 96.0 |
| 26.7 | 64.1 | 9.2 | 0.3 | 5.1 | 94.5 |
| 10.9 | 59.0 | 30.1 | 0.5 | 9.2 | 90.2 |
| 7.4 | 52.6 | 40.0 | 0.8 | 11.4 | 87.8 |
| 47.8 | 50.6 | 1.5 | 0.1 | 2.1 | 97.7 |
| 69.1 | 30.6 | 0.3 | 0.1 | 1.7 | 98.2 |
| 81.5 | 18.2 | 0.3 | 0.1 | 1.1 | 98.8 |

TABLE B

Liquid-Liquid Equilibrium Data for Ethanol-Water-Gasoline at 50° C.

| Tie Lines | Water Phase (weight %) | | | Gasoline Phase (weight %) | | |
| --- | --- | --- | --- | --- | --- | --- |
| | Water | Ethanol | Gasoline | Water | Ethanol | Gasoline |
| (a) | 38.0 | 56.3 | 5.7 | 0.3 | 5.6 | 94.1 |
| (b) | 20.8 | 61.9 | 17.3 | 0.6 | 9.7 | 89.7 |
| (c) | 9.3 | 52.5 | 38.1 | 1.8 | 16.4 | 81.8 |
| (d) | 61.0 | 38.2 | 0.8 | 0.2 | 2.0 | 97.8 |
| (e) | 77.4 | 22.6 | <0.1 | 0.1 | 0.6 | 99.3 |
| (f) | 86.1 | 13.9 | <0.1 | <0.1 | 0.2 | 99.8 |
| (g) | 52.8 | 45.6 | 1.6 | 0.2 | 3.3 | 96.5 |

Similar liquid-liquid equilibrium data can be developed for other specific gasolines. As the aromatic content of the gasoline increases, the solubility of the ethanol in the gasoline tends to increase. This is advantageous from the standpoint of using the gasoline as an extracting solvent for the ethanol, but gasolines of higher aromatic content are more expensive. In general, however, under the conditions set out above, the process of this invention is applicable to any gasoline from very low to very high octane gasolines. On the basis of present information, it is believed that the most advantageous gasolines for use in the process of the present invention are those having a motor octane number of from about 75 to 90. Gasohol products of the desired ethanol concentration can be produced, as illustrated with reference to FIG. 2. The tie lines a to g intersect the phase equilibrium curve at the points shown in Table B. The gasohol point on the equilibrium curve is indicated at approximately 11% by weight ethanol. At that ethanol concentration, it may be estimated from FIG. 2 that the extraction product will contain around 88% gasoline and 1% water by weight.

This invention is further illustrated by the following examples.

EXAMPLE I

Using a fractional distillation column and a counter-current extraction column in a system similar to that shown in FIG. 1, an aqueous fermentation beer of 7.3% by weight ethanol is fed to the distillation column and distilled therein to produce a distillate of approximately 80% ethanol by weight. The distillation column waste will contain less than 0.025% ethanol by weight. If desired the column waste may be used to preheat the feed stock by means of a liquid-liquid indirect heat exchanger, as indicated in FIG. 1. The distillate may be condensed in a condenser to provide liquid reflux for the distillation column and liquid feed for the extraction column, as indicated in FIG. 1. In the illustration given, the condenser is a condenser-heater within which the distillate vapor is condensed by indirect heat exchange with the liquid gasoline extract from the extraction column. This part of the process, however, is optional.

The 80% ethanol by weight feed to the extraction column is contacted therein with a low octane gasoline similar to the gasoline from which the data of Table A and FIG. 2 was obtained. The ethanol-gasoline product will contain approximately 11% ethanol by weight (10% by volume), and will contain approximately 88% gasoline and 1% water. The extractor raffinate will contain around 30% ethanol by weight, and is preferably returned to an intermediate portion of the enriching (rectifying) section of the distillation column, as indicated in FIG. 1. The raffinate is thereby introduced above the lower ethanol concentration feed.

The operating conditions described above are summarized below in Table C. The streams identified by the column headings A to F are further described below the table, and corresponding reference letters have been applied to the streams in FIG. 1.

TABLE C

| Stream | Summary of Operating Conditions | | | | | |
|---|---|---|---|---|---|---|
| | A | B | C | D | E | F |
| wt. % ethanol | 7.3 | 80 | 11 | 0 | 30 | <.025 |
| wt. % water | 92.7 | 20 | 1 | 0 | 70 | — |
| wt. % gasoline | 0 | 0 | 88 | 100 | <1 | 0 |
| Total flow, lbs | 35,607 | 3508 | 23,698 | 20,854 | 664 | 32,760 |
| mol % ethanol | 3 | 61 | — | — | 15 | <.01 |
| mol % water | 97 | 39 | — | — | 85 | >99.99 |
| Total flow, lb mols | 1890 | 100 | — | — | 30 | 1820 |

Stream Indentification: A, aqueous ethanol feed to distillation column; B, aqueous ethanol feed to extractor; C, ethanol-gasoline product (10% by vol. ethanol); D, gasoline feed; E, extractor raffinate; F, distillation column waste.

With further reference to the foregoing operating system, the total number of ideal stages required in the distillation column will depend on the desired ethanol concentration in waste stream F, with a predominantly large share of stages needed below the feed stage. The distillation column can operate with a reflux ratio of about 1.7. With the extractor operating at 50° C., as described, the extractor should be designed to provide between 4 and 5 ideal stages.

EXAMPLE II

For reducing the water content of the gasoline extract (stream C in FIG. 1) a flash distillation and liquid separation system may be used, as illustrated in FIG. 1. The product stream C is heated in the condenser-heater by the condensing distillate and then introduced into a flash drum to produce water-rich vapor phase (stream H) and leaving a liquid phase (stream G) of reduced water content. Vapor stream H is condensed in a condenser and passed to a liquid separator. The flashed vapor (stream H) is of such composition that two liquid phases form on condensation. The gasoline-rich phase, stream I, will be close in composition to the unflashed liquid, stream G, and is combined with this stream to form the gasohol product, as indicated in FIG. 1. The gasoline-lean phase, stream J, is returned to the extraction column at an appropriate stage. It will be understood that such a flash distillation and liquid separation system is optional, since other procedures can be used to dry the gasohol product from the extractor. More generally, therefore, gasoline extract containing from 0.8 to 1.2 weight percent water will be subjected to further processing for removal of water to substantially 0.1 weight percent or less.

I claim:

1. The energy saving process of producing gasoline-ethanol mixtures from aqueous ethanol for motor fuel use, comprising:
   (a) subjecting aqueous ethanol of 1 to 70 weight percent ethanol to fractional distillation and producing an aqueous ethanol distillate of 75 to 95 weight percent ethanol together with at least 5 weight percent water; and without employing an azeotropic ethanol distillation;
   (b) thereafter in a separate step subjecting said distillate containing at least said 5% water to countercurrent multiple stage liquid-liquid extraction with gasoline at a temperature within the range from 20° to 100° C., and producing a gasoline phase extract and a water phase raffinate, said gasoline extract containing from 5 to 17% by weight ethanol.

2. The process of claim 1 in which said aqueous ethanol subjected to fractional distillation has an ethanol content of 1 to 15 weight percent.

3. The process of claim 1 in which said distillate has an ethanol content of 75 to 90 weight percent.

4. The process of claim 1 in which said extraction is carried out at a temperature of from 30° to 60° C., and said gasoline extract phase contains from 8 to 14% ethanol by weight.

5. The energy saving process of producing gasoline-ethanol mixtures from aqueous ethanol for motor fuel use, comprising:
   (a) subjecting aqueous ethanol of 1 to 15 weight percent ethanol to fractional distillation and producing an overhead distillate in vapor form containing 75 to 90 weight percent ethanol together with at least 10 weight percent water;
   (b) condensing said distillate to provide reflux for said distillation column and a feed for a countercurrent multiple stage liquid-liquid extraction column; and without employing an azeotropic ethanol distillation;
   (c) thereafter in a separate step subjecting said condensed distillate containing at least said 10% water in said extraction column to extraction with gasoline at a temperature of from 30° to 60° C. and producing a gasoline phase extract and a water phase raffinate, said gasoline extract containing from 8 to 14% ethanol by weight.

6. The process of claim 5 in which said aqueous ethanol subjected to fractional distillation has an ethanol content of 1 to 15 weight percent.

7. The process of claim 1 or claim 5 in which the raffinate from said extraction column is introduced into the rectifying section of said distillation column.

8. The process of claim 1 or claim 5 in which said gasoline extract contains from 0.8 to 1.2 weight percent water, and said extract is subjected to further processing for removal of water to substantially 0.1 weight percent or less.

9. The process of claim 5 in which the heat removed from said distillate in the condensation thereof is used to heat said gasoline extract for flash distillation thereof to reduce its water content.

* * * * *